United States Patent [19]

Lemanski et al.

[11] Patent Number: 5,334,751
[45] Date of Patent: Aug. 2, 1994

[54] ETHYL ACETATE FROM ETHANOL

[75] Inventors: Michael F. Lemanski, Cleveland; Joseph B. Hazen, Garfield Heights; Patricia R. Blum, Macedonia, all of Ohio

[73] Assignee: The Standard Oil Company, Cleveland, Ohio

[21] Appl. No.: 874,947

[22] Filed: Apr. 28, 1992

Related U.S. Application Data

[63] Continuation-in-part of Ser. No. 624,845, Dec. 10, 1990.

[51] Int. Cl.$^5$ .............................................. C07C 67/02
[52] U.S. Cl. .................................. 560/265; 560/239; 562/538; 502/213
[58] Field of Search ............... 560/265, 239; 562/538; 502/213

Primary Examiner—José G. Dees
Assistant Examiner—Joseph M. Conrad
Attorney, Agent, or Firm—Charles S. Lynch; Michael F. Esposito; David J. Untener

[57] ABSTRACT

Disclosed is a process for making ethyl acetate which comprises reacting in a reaction zone ethyanol and molecular oxygen in the presence of a solid catalyst containing the elements and proportions indicated by the empirical formula $$Pd_aM_bTiP_cO_x \qquad \text{(formula 1)}$$

where M is selected from Cd, Au, Zn, Tl, alkali metals and alkaline
 earth metals,
 a is from 0.0005 to 0.2
 b is from zero to 3a
 c is 0.5 to 2.5, and
 x is a value sufficient to satisfy the valence requirements of
 the other elements present, and
wherein said catalyst contains crystalline $TiP_2O_7$.

2 Claims, No Drawings

ETHYL ACETATE FROM ETHANOL

This application is a continuation-in-part of pending application Ser. No. 624,845, filed Dec. 10, 1990.

The present invention relates to a process for the catalytic oxidation of ethanol to ethyl acetate.

It is an object of the present invention to provide a novel process for the production of ethyl acetate by the oxidation of ethanol with molecular oxygen.

Other objects, as well as aspects, features and advantages, of the present invention will become apparent from a consideration of the specification, including the specific examples and the claims.

These and other objects are achieved by the present invention, wherein there is provided a process for making ethyl acetate which comprises reacting in a reaction zone ethanol and molecular oxygen in the presence of a solid catalyst containing the elements and proportions indicated by the empirical formula $$Pd_aM_bTiP_cO_x \quad \text{(formula 1)}$$

where M is selected from Cd, Au, Zn, Tl, alkali metals and alkaline
 earth metals,
 a is from 0.0005 to 0.2
 b is from zero to 3a
 c is 0.5 to 2.5, and
 x is a value sufficient to satisfy the valence requirements of the other elements present, and
wherein said catalyst contains crystalline $TiP_2O_7$.

The description of the catalyst in the foregoing paragraph means that the overall empirical formula of the catalyst composition is $Pd_aM_bTiP_cO_x$. It also means that part of the Ti and the P in the catalyst which has the above formula is in the form of the crystalline compound $TiP_2O_7$. Whatever $TiP_2O_7$ that is present is not in addition to a catalyst of the above formula but is part of the catalyst of the formula $Pd_aM_bTiP_cO_x$. Thus, the catalyst of the foregoing paragraph can be synonymously described as "a solid catalyst that (1) contains crystalline $TiP_2O_7$ and (2) has the elements and proportions indicated by the empirical formula $$Pd_aM_bTiP_cO_x \quad \text{(formula 1)}$$

where M is selected from Cd, Au, Zn, Tl, alkali metals and alkaline earth metals,
 a is from 0.0005 to 0.2
 b is from zero to 3a
 c is 0.5 to 2.5, and
 x is a value sufficient to satisfy the valence requirements of the other elements present, and
the Ti and P of said crystalline $TiP_2O_7$ represents part of the Ti and P of said formula 1."

In the above formula 1, a is usually from 0,005 to 0.05, more usually from 0.002 to 0.04; and c is usually not less than 0.8 nor more than 2, more often not over 1.25.

When M is used, b is usually at least 0.0001a.

We have found that the crystalline $TiP_2O_7$, titanium pyrophosphate, is not only an effective and mechanically tough physical support for the palladium component of the catalyst, but also contributes to the catalytic activity.

As noted, the catalysts contain crystalline $TiP_2O_7$ in varying amounts. In general, when c in formula 1 is less than 2, the amount or proportion of crystalline $TiP_2O_7$ is lower than if c is 2. The crystalline $TiP_2O_7$ is always present, and to whatever extent it is present it contributes its support function and it contributes to catalytic activity.

The molecular oxygen in the feed to the reaction zone can be pure oxygen gas or, alternatively, an oxygen-containing gas mixture such as air or air enriched with oxygen. In addition to these materials the gaseous feed mixture introduced to the reaction zone in the process can contain inert diluents such as carbon dioxide or nitrogen.

The following catalysts are illustrative of specific catalysts useful in the oxidation process of the invention. They all contain titanium pyrophosphate, $TiP_2O_7$, as a crystalline phase.

In making such catalysts, it is necessary to heat or calcine the composition sufficiently to result in the formation of the necessary $TiP_2O_7$ crystalline phase. This is not accomplished at calcination temperatures up to 200° C. It is accomplished in those specific examples of the invention which are calcined at temperatures of 400° to 850° C. What is not known is the lowest temperature at which $TiP_2O_7$ can be formed below 400° C. and above 200° C., but this can easily be checked by routine trial and error by calcining at various temperatures at various times and then subjecting the resulting calcined composition to X-ray powder diffraction testing to detect the presence of the crystalline compound $TiP_2O_7$.

CATALYST 1

$TiPd_{0.01}K_{0.03}PO_x$

Palladium acetate, $[Pd(OOCCH_3)_2]_3$ (1.114 g) was added to 200 ml of distilled water. This slurry was heated with stirring at about 60°-80° C. for 5 minutes. Then 1.33 g of potassium nitrate was added to the slurry and the heating was continued for 30 minutes. By the end of this time the slurry was dark brown and a portion of the palladium acetate had dissolved. To this slurry was added 52.0 g of 85% $H_3PO_4$, followed by the addition of 36.0 g of titanium dioxide. This slurry was then boiled and dried down to a thick paste. This paste was placed in a drying oven set at 200° C., and dried overnight. The solid was then ground and screened; the 20/35 mesh portion of the solid was calcined in air at 700° C. for 16 hours.

CATALYST 2

$TiPd_{0.04}P_{1.33}O_x$

Palladium acetate (3.71 g) was added to 200 ml of distilled water. This slurry was heated with stirring at about 60°-80° C. for 30 minutes. By the end of this time the slurry was dark brown and a portion of the palladium acetate had dissolved. To this slurry was added 57.8 g of 85% phosphoric acid, followed by the addition of 30.0 g of titanium dioxide. This slurry was then boiled and dried down to a thick paste. This paste was placed in a drying oven at about 110° C., and dried overnight. After drying the solid was ground and screened. The through 20 on 35 mesh portion was calcined in air at 400° C. for 16 hours.

CATALYST 3

$TiPd_{0.02}P_{0.67}O_x$

Palladium acetate (3.71 g) was added to 200 ml of distilled water. This slurry was heated with stirring at about 60°-80° C. for 30 minutes. By the end of this time the slurry was dark brown and a portion of the palladium acetate had dissolved. To this slurry was added 57.8 g of 85% phosphoric acid, followed by the addition of 60.0 g of titanium dioxide. This slurry was then boiled and dried down to a thick paste. This paste was placed in a drying oven at about 110° C., and dried overnight. After drying the solid was ground and screened. The through 20 on 35 mesh portion was calcined in air at 400° C. for 16 hours.

CATALYST 4

$TiPd_{0.03}PO_x$

Palladium acetate (3.71 g) was slurried in 200 ml of distilled water and heated gently ($^{18}60°$ C.) with stirring for 30 min. Phosphoric acid (85%, 57.8 g) was added to the slurry, followed by the addition of titanium dioxide (40.0 g). The slurry was evaporated to a paste on high heat, then dried in air at $^{18}110°$ C. over the week end. The solid was broken into chunks and calcined at 800° C. for 16 hrs. The calcined solid was ground and screened. The portion which passed through 20 mesh but was retained by 35 mesh screens was used for reactor tests.

CATALYST 5

$TiPd_{0.075}PO_x$

In 150 ml of distilled water, 11.58 g of palladium nitrate, 57.8 g of 85% phosphoric acid and 40 g of titanium dioxide were combined. The slurry was evaporated to a thick paste with high heat. The paste was dried overnight at 110° C., ground and screened, and the 20/35 mesh portion was calcined at 400° C., under air for 16 hours.

CATALYST 6

$TiPd_{0.003}PO_x$

The following reagents: 0.3345 g of palladium acetate, 52.0 g of 85% phosphoric acid, and 36.0 g of titanium dioxide were added to 200 ml of distilled water. The mixture was heated at 70° C. for 30 minutes. The heat was then increased and the slurry was evaporated to a thick paste. The paste was dried overnight at 200° C., ground and screened, and the 20/35 mesh portion of the solid was calcined at 700° C., in air for 16 hours.

CATALYST 7

$TiPd_{0.03}K_{0.07}PO_x$

Palladium acetate (2.23 g) was added to 120 ml of distilled water. This slurry was heated with stirring at about 60°-80° C. for 5 minutes. Then 2.07 g of potassium nitrate was added to the slurry and the heating was continued for 30 minutes. By the end of this time the slurry was dark brown and a portion of the palladium acetate had dissolved. To this slurry was added 34.7 g of 85% $H_3PO_4$, followed by the addition of 24.0 g of titanium dioxide. This slurry was then boiled and dried down to a thick paste. This paste was placed in a drying oven set at $^{18}110°$ C., and dried overnight. The solid was then broken into pieces and calcined in air at 800° C. for 8 hours. After calcination the solid was ground to 10/35 mesh particle size range.

CATALYST 8

$TiPd_{0.03}K_{0.07}Cd_{0.03}PO_x$

The procedure was the same as in Catalyst 7 except that immediately after the addition of potassium nitrate, 1.80 g of cadmium acetate was added to the slurry.

CATALYST 9

$TiPd_{0.03}PO_x$ 3.71 g of palladium acetate was slurried in 150 ml of distilled water. The slurry was heated gently ($^{18}60°$ C.) with stirring. Phosphoric acid (85%, 57.8 g) was added to the slurry along with a few drops of acetic acid (to aid solubility). Titanium dioxide (40.0 g) was then added, and slurry was evaporated to a paste using high heat on the hot plate. The paste was dried at 110° C. in air over the weekend. The dried solid was ground and screened. The portion which passed through 20 mesh but was retained on 35 mesh screens was calcined at 400° C. for 20 hrs in air.

CATALYST 10

$TiPd_{0.03}Ca_{0.07}PO_x$

Palladium acetate (3.71 g) and calcium nitrate.$XH_2O$ (6.58 g) were added to 200 ml of distilled water. This slurry was heated with stirring at about 60°-80° C. for 30 minutes. To this slurry was added 57.8 g of 85% $H_3PO_4$, followed by the addition of 40.0 g of titanium dioxide. This slurry was then boiled and dried down to a thick paste. This paste was placed in a drying oven set at 200° C., and dried overnight. The solid was then ground and screened to produce a 10/35 mesh portion. This 10/35 mesh portion was calcined in air at 800° C. for 16 hours.

CATALYST 11

$TiPd_{0.03}Na_{0.06}PO_x$

The procedure is the same as in example 10 except 2.53 of sodium nitrate is used instead of the calcium nitrate.

The following specific examples of oxidation runs of the invention were carried out in a stainless steel tubular-reactor containing a fixed bed of the designated particulate catalyst. The reactor was equipped with a central thermowell within which a thermocouple could be variably positioned in order to probe the temperature of the catalyst bed under reaction conditions. The reactor was fitted into an electrically heated, suitcase-type furnace. Gaseous feeds to the reactor were controlled by electronic mass flow controllers; liquid feeds were pumped to the reactor using a Waters Model 590 liquid chromatograph pump. They were vaporized prior to contacting the catalyst bed. Feeds were passed through the reactor in the downflow configuration.

Catalyst was in the form of particles ground to size, 0.35-1.68 mm in diameter (the fraction which passed through 10 mesh but not 40 mesh). The reactor effluent was passed through a distilled water scrubber which was chilled with ice in order to dissolve all liquid products. The liquid scrubber sample was analyzed for ethanol, ethyl acetate, and acetic acid using a cross-linked methyl silicone capillary column in a Hewlett-Packard gas chromatograph. Acetic acid was also quantitated via titration using a Brinkman 665 Dosimat and 686 Titroprocessor.

It is noted that acetic acid is often obtained as a valuable by-product or co-product in addition to the ethyl acetate.

While the particular temperatures and pressures are not the essence of the invention, it should be noted that pressures of zero to 400 psig (and higher), temperatures of 150° to 250° C. for example can be used. Also, as the temperature, and especially as the pressure, is raised, it becomes increasingly difficult to control the exotherm, to the point that a runaway reaction can occur. In that event, the addition of a moderator element M of formula 1, or lowering the concentration of Pd in the catalyst composition, or both, generally tends to allow the use of higher reaction zone operating pressures while avoiding an uncontrollable reaction zone temperature increase.

EXAMPLE 1

In this oxidation example Catalyst 4 was used. The reaction zone temperature and pressure were 180° C. and 0 psig, respectively, contact time was 1.56 seconds and the feed stream contained ethanol/oxygen/nitrogen in the ratios 1:2.22:22.11. Conversion of ethanol was 41.63%. Yields of ethyl acetate and acetic acid were 24.9% and 15.0%, respectively.

EXAMPLE 2

In this oxidation example Catalyst 4 was used. The reaction zone temperature and pressure were 200° C. and 0 psig, respectively, contact time was 1.50 seconds and the feed stream contained ethanol/oxygen/nitrogen in the ratios 1:2.22:22.11. Conversion of ethanol was 95.94%. Yields of ethyl acetate and acetic acid were 46.7% and 37.1% respectively.

EXAMPLE 3

In this oxidation example Catalyst 4 was used. The reaction zone temperature and pressure were 225° C. and 0 psig, respectively, contact time was 1.42 seconds and the feed stream contained ethanol/oxygen/nitrogen in the ratios 1:2.24:22.34. Conversion of ethanol was 98.58%. Yields of ethyl acetate and acetic acid were 24.3% and 54.2%, respectively.

EXAMPLE 4

In this oxidation example Catalyst 9 was used. The reaction zone temperature and pressure were 200° C. and 0 psig, respectively, contact time was 1.47 seconds and the feed stream contained ethanol/oxygen/nitrogen/steam in the ratios 1:1.75:14.2:3.08. Conversion of ethanol was 97.61%. Yields of ethyl acetate and acetic acid were 14.8% and 75.5%, respectively.

EXAMPLE 5

In this oxidation example Catalyst 4 was used. The reaction zone temperature and pressure were 150° C. and 0 psig, respectively, contact time was 1.67 seconds and the feed stream contained ethanol/oxygen/nitrogen in the ratios 1:2.24:22.34. Conversion of ethanol was 48.63. Yields of ethyl acetate and acetic acid were 17.1% and 31.5%, respectively.

As will be evident to those skilled in the art, various modifications of this invention can be made or followed in the light of the foregoing disclosure and discussion without departing from the spirit and scope of the disclosure or from the scope of the claims.

We claim:

1. A process for making ethyl acetate which comprises reacting in a reaction zone ethanol and molecular oxygen in the presence of a solid catalyst that (1) contains crystalline $TiP_2O_7$, titanium pyrophosphate, and (2) has the elements and proportions indicated by the empirical formula $$Pd_aM_bTiP_cO_x \qquad \text{(formula 1)}$$

where M is selected from Cd, Au, Zn, Tl, alkali metals and alkaline earth metals, a is from 0.0005 to 0.2 b is from zero to 3a c is 0.5 to 2.5, and x is a value sufficient to satisfy the valence requirements of the other elements present, and the Ti and P of said crystalline $TiP_2O_7$ represents part of the Ti and P of said formula 1.

2. A process of claim 1 wherein c is in the range from 0.8 to 2.

* * * * *